US008871279B2

(12) United States Patent
Cheng et al.

(10) Patent No.: US 8,871,279 B2
(45) Date of Patent: Oct. 28, 2014

(54) USE OF THE COMBINATION OF PHY906 AND A TYROSINE KINASE INHIBITOR AS A CANCER TREATMENT REGIMEN

(75) Inventors: Yung-Chi Cheng, Woodbridge, CT (US); Shwu-Huey Liu, Madison, CT (US); Zaoli Jiang, Woodbridge, CT (US); Robert Tilton, Guilford, CT (US)

(73) Assignee: Yale University, New Haven, CT (US)

( * ) Notice: Subject to any disclaimer, the term of this patent is extended or adjusted under 35 U.S.C. 154(b) by 677 days.

(21) Appl. No.: 12/997,513

(22) PCT Filed: Jun. 10, 2009

(86) PCT No.: PCT/US2009/046875
§ 371 (c)(1),
(2), (4) Date: Aug. 2, 2011

(87) PCT Pub. No.: WO2009/152228
PCT Pub. Date: Dec. 17, 2009

(65) Prior Publication Data
US 2012/0009282 A1 Jan. 12, 2012

Related U.S. Application Data

(63) Continuation-in-part of application No. 12/527,302, filed as application No. PCT/US2008/053965 on Feb. 14, 2008, which is a continuation-in-part of application No. 11/100,433, filed on Apr. 7, 2005, which is a continuation-in-part of application No. 10/220,876, filed as application No. PCT/US01/07353 on Mar. 8, 2001, which is a continuation-in-part of application No. 09/522,055, filed on Mar. 9, 2000.

(60) Provisional application No. 61/060,348, filed on Jun. 10, 2008, provisional application No. 60/901,310, filed on Feb. 15, 2007, provisional application No. 60/625,943, filed on Nov. 9, 2004.

(51) Int. Cl.
*A61K 36/00* (2006.01)

(52) U.S. Cl.
USPC .......................................... 424/725; 424/766

(58) Field of Classification Search
USPC ................................................ 424/725, 766
See application file for complete search history.

(56) References Cited

U.S. PATENT DOCUMENTS 4,613,591 A 9/1986 Aburada et al.
4,618,495 A 10/1986 Okuda et al.
(Continued)

FOREIGN PATENT DOCUMENTS

EP 0943620 A2 9/1999
JP 7118161 A 5/1995
(Continued)

OTHER PUBLICATIONS

Morin, Michael J. Oncogene 19.56 (Dec. 27, 2000): 6574-83.*
(Continued)

*Primary Examiner* — Patricia Leith
(74) *Attorney, Agent, or Firm* — Kenyon & Kenyon LLP

(57) ABSTRACT

This invention provides herbal compositions useful for increasing the therapeutic index of chemotherapeutic compounds. This invention also provides methods useful for improving the quality of life of an individual undergoing chemotherapy. Furthermore, this invention improves the treatment of cancer by administering the herbal composition PHY906 in combination with one or more chemotherapeutic compounds to a mammal undergoing such chemotherapy.

24 Claims, 1 Drawing Sheet

(56) References Cited

U.S. PATENT DOCUMENTS

| | | | |
|---|---|---|---|
| 5,414,015 | A | 5/1995 | Konoshima et al. |
| 5,437,866 | A | 8/1995 | Sun |
| 5,595,756 | A * | 1/1997 | Bally et al. ............... 424/450 |
| 5,665,393 | A | 9/1997 | Chen et al. |
| 6,048,847 | A | 4/2000 | Ramadoss et al. |
| 6,630,176 | B2 | 10/2003 | Li et al. |
| 2003/0207270 | A1* | 11/2003 | Kung et al. ............... 435/6 |
| 2005/0196473 | A1 | 9/2005 | Cheng et al. |
| 2007/0280944 | A1* | 12/2007 | Robbins et al. ........... 424/145.1 |
| 2009/0175869 | A1* | 7/2009 | Holmlund et al. ......... 424/138.1 |
| 2010/0189683 | A1* | 7/2010 | Holmlund et al. ......... 424/85.2 |

FOREIGN PATENT DOCUMENTS

| | | |
|---|---|---|
| WO | WO 01/66123 | 9/2001 |
| WO | WO 2006/053049 | 5/2006 |
| WO | WO 2008/101079 | 8/2008 |

OTHER PUBLICATIONS

Wikipedia: Sunitinib, Online, URL<http://web.archive.org/web/20060913000000/http://en.wikipedia.org/wiki/Sunitinib> Sep. 2006, one page.*

Liu, Shwu Huey et al., "Prevention of CPT-11 Induced Toxicity by a Chinese Medicinal Formulation, PHY-906", Proceedings of the American Association for Cancer Research Annual, No. 41, Mar. 2000, p. 410.

Liu, Shwu Huey et al., "A Chinese Medicine Formulation, PHY-906, Can Enhance the Therapeutic Index of CPT-11 and other Anticancer Druges Against Cancer in Mice", Proceedings of the American Association for Cancer Research Annual, vol. 42, Mar. 2001, p. 85.

M. Narita et al., "Inhibition of Beta-Glucuronidase by Natural Glucurondes of Kampo Medicines Using Glucuronide of SN-38(7-Ethyl-10-Hydroxycamptothecin) as a Substrate", Xenobiotia, vol. 23, No. 1, 1993, p. 5-10.

Takasuna et al., "Protective Effects of Kampo Medicines and Baicalin Against Intestinal Toxicity of a New Anticancer Camptothecin Derivative, Irinotecan Hydrochloride (CPT-11), in Rats", Japanese Journal of Cancer Research, vol. 86, No. 10, 1995, p. 978-984.

K. Mori et al., "Kampo Medicines for the Prevention of Irinotecan-Induced Diarrhea in Advanced Non-Small cell Lung Cancer", Gan T. Kagaku Ryoho Japanese Journal of Cancer and Chemotherapy, Jul. 1998, 25(8): 1159-1163.

R.M. Goldberg et al., "IrinotecanPlus 5-Fu and Leucovorin in Advanced Colorectal Cancer: North American Trials", Oncology, S. Karger Ag, Basel, CH, vol. Suppl. 6. No. 6, Aug. 1998, p. 59-63.

Bleiberg H., European J. of Cancer, 35(3): 371-379, 1999.

Govindarajan et al., Lancet, 356:566, Aug. 12, 2000.

Stucky-Marshall L., Cancer Nursing, 22(3):212, 1999.

Suzuki et al, Supressor Macrophages: A Role on the Growth of Transplanted Tumors and Regulation by an Extract of Licorice, Glycyrrhizin; Oncologia (Tokyo) 1987, 20(5), pp. 124-133 (abstract).

Raskin et al., "Can an Apple a Day Keep the Doctor Away?" Current Pharmaceutical Design, 2004, 10; pp. 3419-3429.

H.B. MacPhillamy; Plant Science Bulletin; Apr. 1963, vol. 9, Issue 2, pp. 1-15.

Liu, Shwu Huey et al., "Developing PHY-906 as a Broad-Spectrum Modulator of Chemotherapeutic Agents in Cancer Therapy", Proceedings of the Annual Meeting of the American Association for Cancer Research, vol. 45, Mar. 2004, p. 128.

Nagai et al., "Antiviral Activity of Plant Flavonoid, 5,7,4'-Trihydrozy-8-methoxyflavone, from the Roots of *Scutellaria baicalensis* against Influenza A (H3N2) and B Viruses", T et al., Biol Pharm Bull, 1995, 18(2): 295-9.

Huang, L et al., Zhonggou Zhong Yao Za Zhi, 1990, 15(2): 115-7, 128.

Smorl'ianinov, ES et al., Eksp Klin Farmakol, 1997, 60(6): 49-51.

Hande, et al., "Metabolism and Excretion of Etoposide in Isolated, Perfused Rat Liver Models", Cancer Res. 1988, vol. 48, No. 20, p. 5692-5695.

Sommadossi, et al., "Modulation of 5-Fluorouracil Catabolism in Isolated Rat Hepatocytes with Enhancement of 5-Fluorouracil Glucoronide Formation", Cancer Res. 1985, vol. 45, No. 1, p. 116-121.

Certain Chinese Herbal Medicine Prescriptions, 1979.

Yogatrangini by Trimalla Bhatta—Commentary by Duttarama Mathura; Chaukhamba Vidyabhavan, Varanasi, Edn. Reprint 2003, p. 169; F.ID: RG/4478; Form.name: Badarikalkah ("Third party observation" re EP2005826289).

Bogar 700 by Bogar, Ed. Ramachandran, Pub: Thamarai Noolagam Chennai (1994), p. 8-13; F.ID: PD03/02; Form.name: Maha Mega Rasangam ("Third party observation" re EP2005826289).

Li, Ronghua et al.,"Evaluation of Clinical Efficacy and Review on Progress of Antineoplastic Drugs," Evaluation and Analysis of Drug-use in Hospital of China, 2004, vol. 4, No. 1 (in Chinese language, English language abstract).

Li, Dong, "Progress on Clinical Application of Thalidomide," Chinese Journal of Clinical Pharmacy, 2004, vol. 13, No. 2.

Saif, M. W., et al., Phase I study of the botanical formulation PHY906 with capecitabine in advanced pancreatic and other gastrointestinal malignancies. Phytomedicine (2010), doi:10.1016/j.phymed.2009.12.016.

Yen, Y., et al., Phase I/II Study of PHY906/Capecitabine in Advanced Hepatocellular Carcinoma, Anticancer Research 29: 4083-4092 (2009).

* cited by examiner

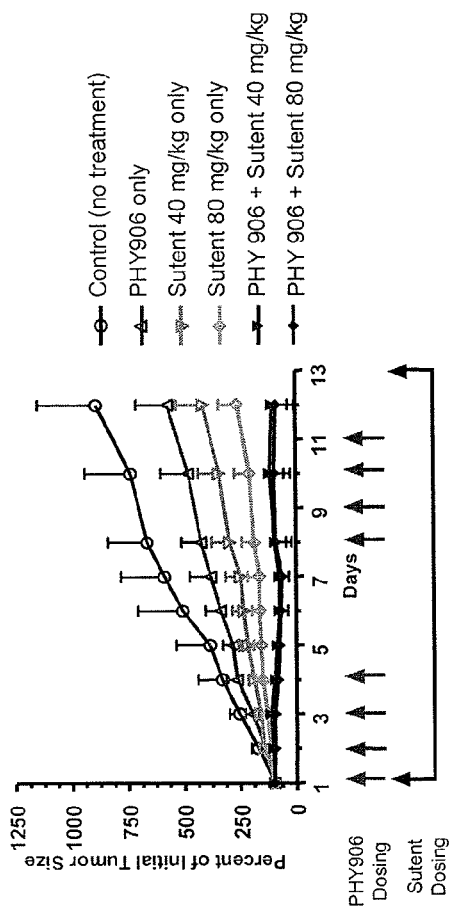

USE OF THE COMBINATION OF PHY906 AND A TYROSINE KINASE INHIBITOR AS A CANCER TREATMENT REGIMEN

CROSS-REFERENCE TO RELATED APPLICATIONS

This application is a U.S. National Stage application of International Application Number PCT/US2009/046875, filed Jun. 10, 2009, which claims the benefit of U.S. Provisional Application No. 61/060,348, filed Jun. 10, 2008 and entitled "Use of the Combination of PHY906 and Sutent® as a Cancer Treatment Regimen", the content of which is herein incorporated by reference in its entirety for all purposes. This application also claims the benefit under 35 U.S.C. §120 as a Continuation-in-Part application of U.S. patent application Ser. No. 12/527,302, filed Aug. 14, 2009, which is a U.S. National Stage application of International Application number PCT/US2008/053965, filed Feb. 14, 2008, which claims the benefit of U.S. Provisional Patent Application Ser. No. 60/901,310, filed on Feb. 15, 2007, which in turn, claims the benefit under 35 U.S.C. §120 as a Continuation-in-Part application of U.S. patent application Ser. No. 11/100,433 filed Apr. 7, 2005, now U.S. Pat. No. 7,534,455, which claims the benefit of U.S. Provisional Patent Application Ser. No. 60/625,943 filed Nov. 9, 2004, and which also claims the benefit under 35 U.S.C. §120 as a Continuation-in-Part of U.S. patent application Ser. No. 10/220,876 filed Sep. 6, 2002, now U.S. Pat. No. 7,025,993, which is a U.S. National Stage application of International Application No. PCT/US2001/007353 filed Mar. 8, 2001, which in turn, is a Continuation-in-Part of U.S. patent application Ser. No. 09/522,055 filed Mar. 9, 2000, the contents of each of which are herein incorporated by reference in their entirety for all purposes. This application is also related to International Application No. PCT/US2005/040605 filed Nov. 9, 2005, the contents of which are herein incorporated by reference in its entirety.

FIELD OF THE INVENTION

The present invention relates to use of herbal compositions for enhancing the therapeutic effects of chemotherapeutic compounds in the treatment of various forms of cancer.

BACKGROUND OF THE INVENTION

Cancer remains one of the major causes of death around the world. Worldwide, more than one-eighth of all deaths are caused by cancer[1]. In the developed countries, cancer follows only coronary diseases as the leading cause of death and is third after coronary and diarrheal diseases in developing countries. It was estimated that more than 12 million new cases of cancer and 7.6 million deaths from cancer occurred worldwide in 2007. The types of cancer that are most prevalent throughout the world varies by geographic region. For example, worldwide, breast cancer is the most frequently diagnosed cancer in women. Depending on the geographic location, female breast cancer incidence rates for 2002 vary to the extent of more than 25-fold. For example, North America, Australia, and Northern and Western Europe have the highest incidence of breast cancer; intermediate levels are reported in Eastern Europe. Large parts of Africa and Asia have the lowest rates.

Although the understanding of the causes of cancer and the development of methods to treat the disease have evolved over the past 40 years or so, there are still many forms of the disease which respond poorly to treatment. Specifically, advanced hepatocellular carcinoma (also known as, HCC or primary liver cancer) and pancreatic cancer are two examples of malignancies for which current treatments are far from satisfactory. Treatment of cancer can involve many modalities including surgery, radiation treatment, chemotherapy, and combinations of these. The choice of treatment and the success of the treatment are dictated by the type of cancer, the stage of the disease, and whether or not previous treatments have been used.

SUMMARY OF THE INVENTION

In one embodiment, the present application provides a composition comprising: i) a pharmaceutically acceptable carrier; ii) an herbal preparation comprising *Scutellaria, Glycyrrhiza, Ziziphus,* and *Paeonia*; and iii) one or more chemotherapeutic compounds.

In another embodiment, the present application provides a method of treating cancer in a mammal in need thereof comprising administering a therapeutically effective amount of a composition to the mammal comprising: i) a pharmaceutically acceptable carrier; ii) an herbal preparation comprising *Scutellaria, Glycyrrhiza, Ziziphus,* and *Paeonia*; and iii) a chemotherapeutic formulation comprising a chemotherapeutic compound.

BRIEF DESCRIPTION OF THE DRAWING

FIG. 1 shows the effect of PHY906 on tumor growth in Sutent®-treated NCr nude mouse bearing HepG2 tumors.

DETAILED DESCRIPTION OF THE INVENTION

Mixtures of botanical extracts have been widely used throughout the world for the management of disease and are gaining increased acceptance in Western countries[2-5]. The use of Traditional Chinese Medicine (TCM) is based on many chemical components in an herbal preparation that interact and act simultaneously through multiple molecular targets and cellular mechanisms. These multiple components serve various functions; some may be responsible for efficacy while others may decrease toxicity or increase bioavailability. Chinese herbal formulations are perhaps the best-known botanical medicines to have been derived from empirical observations in humans over the millennia. The claimed indication of a given Chinese medicinal preparation is sometimes multiple rather than single. This is not surprising since many phytochemical ingredients in a formulation can exert actions at multiple targets and biological pathways.

PHY906, a decoction of a mixture including four herbs, was established more than 1500 years ago for the treatment of diarrhea, abdominal spasms, fever, headache, vomiting, nausea, extreme thirst, and subcardial distention[6]. Our studies showed that PHY906 not only reduced chemotherapy-induced toxicities, including body weight loss and mortality, but it also enhanced the antitumor efficacy of a broad-spectrum of anticancer agents.

In one embodiment, the four herbs that constitute PHY906 are *Scutellaria baicalensis* Georgi (scute baical skullcap root), *Paeonia lactiflora* Pall. (white peony root), *Glycyrrhiza uralensis* Fisch. (licorice root), and *Ziziphus jujube* Mill. (date fruit); with a ratio of 1.5:1:1:1, respectively. Each of the four herbs of PHY906 is reported to possess a distinct pharmacological profile; these include anticancer and antiviral activity, hematological and immunological stimulation, analgesic activity, liver protection, and appetite improvement[7].

PHY906 has proven to be efficacious in enhancing the therapeutic indices of a variety of anticancer agents including, but not limited to CPT-11, 5-FU, CPT-11/5-FU/LV, VP-16, L-OddC and oxaliplatin/5-FU/LV in colorectal cancer; sorafenib, capecitabine, thalidomide, and CPT-11 in liver cancer; and capecitabine, oxaliplatin, gemcitabine and gemcitabine/oxaliplatin in pancreatic cancer in vivo animal models. For example, PHY906 has proven to be a useful adjunct of Camptosar® (CPT-11, irinotecan) for the treatment of advanced colorectal cancer. CPT-11 is a water-soluble derivative of camptothecin (an antitumor alkaloid isolated from *Camptotheca acuminata*) that exhibits a wide spectrum of antitumor activity because of its inhibition of DNA topoisomerase I[8]. CPT-11 is a component of some of the most widely used chemotherapy treatment regimens (e.g. the "Saltz" regimen [CPT-11 plus 5-fluorouracil/leucovorin], IFL, FOLFIRI, AIO) for colorectal cancer[9,10]. Diahrrea has long been recognized as one of the most common limiting side effects associated with CPT-11 use, regardless of the schedule of administration[11-13]. It causes two types of diarrhea: (a) early acute diarrhea that occurs soon after CPT-11 administration and (b) late-onset diarrhea that occurs usually after an average period of 6 days. In about 40% of patients, this side effect is classified grade 3 (serious) or grade 4 (life-threatening) according to the National Cancer Institute Common Toxicity criteria[14]. High-dose loperamide is considered standard treatment for CPT-11-induced diarrhea in Europe and the US, but the success of this approach is limited[15].

In preclinical studies, when PHY906 was used in combination with CPT-11 in mice bearing Colon 38 tumors, the antitumor efficacy of the combination was greater than that of CPT-11 alone, and the toxicity (as measured by body weight loss and mortality) seen with PHY906+CPT-11 was reduced over that seen with CPT-11 alone[16]. Although the effects of PHY906 on CPT-induced diarrhea were not directly measured, the reduction by PHY906 of body weight loss induced by CPT-11 acts as a "surrogate" marker for diarrhea reduction. In mice bearing Colon 38 tumors and treated with a high dose of CPT-11, PHY906 proved to be much more effective in reducing body weight loss than other "antidiarrheals" including loperamide and the Chinese herbal formulations TJ-14ST, TJ-15, and PHY915[17].

On the basis of the above, and other, preclinical studies, an FDA-approved, Phase I/IIa, multicenter, randomized, double-blind, placebo-controlled, cross-over dose escalation, safety study in patients with advanced, refractory colorectal cancer in which the combination of CPT-11 plus 5-fluorouracil/leucovorin (5-FU/LV) supplemented by PHY906 or placebo was used as first-line treatment, was launched in 2002. The trial was terminated earlier than expected when the oncology community in the United States adopted a new first-line chemotherapy that included the agent Eloxatin® (oxaliplatin) for advanced colorectal cancer and patient recruitment rates slowed. PHY906 was shown to be safe with no serious adverse events (SAEs) attributed to the study drug. PHY906 was found to have no appreciable effect on the metabolism of CPT-11 or 5-FU in controlled metabolic testing (pharmacokinetic study). Fifteen of seventeen patients treated showed either a partial response or stable disease after two courses of treatment. Reduction of diarrhea/nausea/vomiting induced by CPT-11 treatment was observed in the cross-over, internal, patient controls. PHY906 reduced the amount of loperamide necessary to treat CPT-11-induced diarrhea. At a dose of 1.2 g/day, PHY906 reduced the severity of diarrhea by one grade and, at a dose of 2.4 g/day, it reduced nausea/vomiting by one grade[18,19].

Recently, a Phase I/II study of the use of PHY906 in combination with the chemotherapeutic agent Xeloda® (capecitabine) in patients with advanced hepatocellular carcinoma (HCC, primary liver cancer)[20]. Both doses of PHY906 (600 mg or 800 mg given orally twice per day on days 1-4 and days 8-11) with capecitabine (750 mg/m$^2$ given orally twice per day on days 1-14) were well tolerated in HCC patients. The dosing regimen of PHY906 (800 mg given orally twice per day on days 1-4 and days 8-11) with capecitabine (750 mg/m$^2$ given orally once per day on days 1-14) was used in the Phase II study. The results of the study were (N=the number of patients): (a) among 27 evaluable HCC patients in US sites, 14.8% (N=4) achieved minor response, 51.9% (N=14) had stable disease, and 33.3% (N=9) had progressive disease at the end of two treatment cycles; (b) the median survival time was 9.2 months (N=27) for all patients; (c) for Child-Pugh A patients (N=20), median survival time was 10.9 months; (d) Asian patients (N=12) had a higher median overall survival time (16.5 months) than non-Asian patients (6.2 months, N=15) [p=0.03]. In addition, the severity of side effects, particularly diarrhea and fatigue, in this study were much lower than those reported in the pivotal Phase III study used for the FDA approval of Nexavar® for HCC.

Hepatocellular carcinoma (HCC primary liver cancer), a common tumor worldwide, with a varying geographic incidence, is frequently encountered in Southeast Asia and sub-Saharan Africa[25,26]. Once considered a rare tumor in the United States (U.S.), Western Europe, and Australia, its incidence has been rising in the U.S. In fact, a 48% increase in the incidence of hepatobiliary cancers has occurred between the years 1993 and 2000 from 15,000 to 20,200 in the year 2000[27,28]. Indeed, El-Serag and Mason have recently reported an increase in the incidence of HCC in the United States, mostly in the African-American population[3]. Until recently, there was no FDA-approved treatment for this disease. In late 2007, Nexavar® (sorafenib), a multiple tyrosine kinase inhibitor[31] previously approved for the treatment of renal cell cancer, was approved for the treatment of advanced unresectable HCC[30]. However, advanced HCC remains one of the most difficult to treat cancers.

Sutent® is an oral, small-molecule, multi-targeted receptor tyrosine kinase inhibitor. A tyrosine kinase is an enzyme that can transfer a phosphate group from ATP to a tyrosine residue in a protein. Thus, a tyrosine kinase inhibitor interferes with cell communication and growth and may prevent tumor growth. Sutent® is the malate salt of sunitinib; i.e., sunitinib malate. The active ingredient of Sutent® is sunitinib, the chemical name of which is N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide. The terms "Sutent®" and "sunitinib" are used interchangeably throughout this application. In early 2006, Sutent® was approved by the FDA for the treatment of renal cell carcinoma and gastrointestinal stromal tumors that are resistant to treatment with Gleevec®. Sunitinib was the first cancer drug simultaneously approved for two different indications[21]. Sunitinib has become the standard of care for both of these cancers, and is currently being studied for the treatment of many others.

Sutent® acts by inhibiting cellular signaling through its targeting of multiple receptor tyrosine kinases[22-24]. These include all platelet-derived growth factor receptors and vascular endothelial growth factor receptors which play a role in both tumor angiogenesis and tumor cell proliferation. The simultaneous inhibition of these targets leads to both reduced tumor vascularization, cancer cell death, and tumor shrinkage.

A study was conducted in which immune-deficient NCr "nude" mice bearing HepG2 (human hepatocellular carcinoma) tumors were treated with PHY906 alone, Sutent® alone, or with the combination of PHY906 and Sutent®. PHY906 was administered twice per day at a dose of 500 mg/kg for four days beginning on day 1, and was continued on a 4 days on, 3 days off schedule. Sutent® was given once per day. Two doses of Sutent® were used, 40 mg/kg and 80 mg/kg. As can be seen in FIG. 1, PHY906 by itself had slight effect on the tumor growth rate over the 10-day period of observation. Sutent® alone significantly reduced the tumor growth rate at both doses employed with the 80 mg/kg dose being the most effective. When the combination of PHY906 and Sutent® was used, not only was the growth of the tumors stopped, but the size of the tumors appeared to be decreased from pretreatment levels by five days and the rate of tumor growth appeared to remain depressed for the 10-day period; this observation was seen at both doses of Sutent®.

It can be concluded that (a) PHY906 potentiates the anti-tumor activity of Sutent®, and (b) the combination of PHY906 and Sutent® is very effective as a chemotherapeutic treatment in this liver cancer animal model system.

The positive results from these preclinical studies demonstrate that PHY906 can be used as an adjuvant for a broad-spectrum of different types of chemotherapeutic agents in anti-cancer therapy. The cancers include, but are not limited to, colorectal cancer, liver cancer, hepatocellular carcinoma, and pancreatic cancers. The methods of the present invention can be used to improve the quality of life of patients including mammals under chemotherapy. Specifically, this invention relates to the dosing and scheduling of PHY906 in potentiating the therapeutic index of a broad-spectrum of cancer chemotherapeutic agents by the herbal composition PHY906.

All applications, patent, and publications referenced herein are incorporated by reference to the same extent as if each individual application, patent, and publication was specifically and individually indicated to be incorporated by reference. Specifically, the disclosures of WO 01/66123, WO 06/053049, U.S. Pat. No. 7,025,993, US 2005/0196473, and US 2003/0211180 are incorporated herein by reference in their entirety for all purposes. Furthermore, the following references and their contents are herein incorporated by reference in their entirety for all purposes:

REFERENCES

1. Garcia M, Jemal A, Ward E M, Center M M, Hao Y, Siegel R L, Thun M J. *Global Cancer Facts & Figures 2007*. Atlanta, Ga.: American Cancer Society, 2007.
2. Okada F (1996). *Kampo medicine: a source of drugs waiting to be exploited*. Lancet 348:5-6.
3. Ernst E, Pittler M H (2002). *Herbal Medicine*. Med Clin North Amer 86:149-161.
4. Cheng Y C (2001). *What it takes to bring herbal medicine into mainstream medicine of the 21st century: a personal perspective*. Life Resource Publ. Co., Hong Kong. pp. 27-35.
5. Wong R, Sagar C M, Sagar S M (2001). *Integration of Chinese medicine into supportive cancer care: a modern role for an ancient tradition*. Cancer Treat Rev 27:235-246.
6. Hsu H Y, Hsu C S (1980). *Commonly Used Chinese Herb Formulas—with illustrations*. Oriental Healing Art Inst., Los Angeles.
7. *Chinese Botany* (1999): Shanghai Science and Technology Publ., Shanghai, 2$^{nd}$ ed., Vol 7.
8. Kawato Y, Aonuma M., Hirota Y, et al. (1991). *Intracellular roles of SN-38, a metabolite of the camptothecin derivative, in the antitumor effect of CPT-11*. Cancer Res 51:4187-4191.
9. Saltz L B, Cox J V, Blanke C, et al. (2000). *Irinotecan plus fluorouracil and leucovorin for metastatic colorectal cancer*. New Engl J Med 343:905-914.
10. *Colon Cancer (PDQ®): Treatment—Health Professional Version*. National Cancer Institute, U.S. National Institutes of Health Website, updated April.
11. Cunningham D, Pyrrhonen S, James R, et al. (1998). *Randomized trial of irinotecan plus supportive care versus supportive care alone after fluorouracil failure for patients with metastatic colon cancer*. Lancet 352:1413-1418.
12. Rougier P, Bugat R, Douillard J Y, et al. (1997). *Phase II study of irinotecan in the treatment of advanced colorectal cancer in chemotherapy-naïve patients and patients pretreated with fluorouracil-based chemotherapy*. J Clin Oncol 15:251-260.
13. Sargent D J, Niedzwiecki D, O'Connell M J, Schilsky R L (2001). *Recommendation for caution with irinotecan, fluorouracil, and leucovorin for colorectal cancer*. New Engl J Med 345:144-145.
14. Hecht J R (1998). *Gastrointestinal toxicity of irinotecan*. Oncology 12:72-78.
15. Rothenberg M L, Cox J V, DeVore R F, et al. (1999). *A multicenter, phase II trial of weekly irinotecan (CPT-11) in patients with previously treated colorectal carcinoma*. Cancer 85:786-795.
16. Liu S H, Jiang Z, Cheng Y C (2001). *A Chinese medicine formulation, PHY906 can enhance the therapeutic index of CPT-11 and other anticancer drugs against cancer in mice*. Proc Amer Assoc Cancer Res 42:458.
17. Liu S H, Jiang Z, Liddil J, et al. (2000). *Prevention of CPT-11 induced toxicity by a Chinese medicinal formulation, PHY-906*. Proc Amer Assoc Cancer Res 41:2608.
18. Farrell M P, Kummar S (2003). *Phase I/IIA randomized study of PHY906, a novel herbal agent, as a modulator of chemotherapy in patients with advanced colorectal cancer*. Clin Colorectal Cancer 2:253-256.
19. Chu E, Yen Y, Rose M, et al. (2006). *PHY906 in advanced colorectal and hepatocellular cancer clinical trials*. Proc Fifth Mtg of Consortium for Globalization of Chinese Medicine p. 52.
20. Yen Y, So S, Rose M, Saif M W, Chu E, Liu S-H, Foo A, Tilton R, Cheng Y-C (2008). *Phase I/II multicenter study of PHY906/capecitabine in hepatocellular carcinoma*. J Clin Oncol 26: May 20 suppl, abstr 4610.
21. US Food and Drug Administration. *FDA approves new treatment for gastro-intestinal and kidney cancer*.
22. Abrams T J, Lee L B, Murray L J, Pryer N K, Cherrington J M (2006). *SU11248 inhibits KIT and platelet-derived growth factor receptor beta in preclinical models of human small cell lung cancer*. Molec Cancer Ther 2:471-478.
23. Mendel D B, Laird A D, Xin X, et al. (2003). *In vivo antitumor activity of SU11248, a novel tyrosine kinase inhibitor targeting vascular endothelial growth factor and platelet-derived growth factor receptors: determination of a pharmacokinetic/pharmacodynamic relationship*. Clin Cancer Res 9:327-337.
24. O'Farrell A M, Abrams T J, Yuen H A, et al. (2003). *SU11248 is a novel FLT3 tyrosine kinase inhibitor with potent activity in vitro and in vivo*. Blood 101:3597-3605.
25. Parkin D M, Pisani P, Ferlay J (1985). *Estimates of the worldwide incidence of eighteen major cancers in 1985*. Int J Cancer 54:1-13.

26. Parkin D M, Muir C S, Whelan S L, et al. (1992). *Cancer incidence of five continents*. IARC Sci Pub 120:45-173.
27. Boring C C, Squires T S, Tong T, et al. (1995). *Cancer statistics*. CA Cancer J Clin 44:7-26.
28. Greenlee R T, Murray T, Bolden S, and Wingo P A (2000). *Cancer statistics*. CA Cancer J Clin 50:27-33.
29. El-Serag H B, Mason A C (1999). *Rising incidence of hepatocellular carcinoma in the United States*. New Engl J Med 340:745-750.
30. United States Food and Drug Administration (2007). *FDA approves Nexavar for patients with inoperable liver cancer*.
31. Wilhelm S M, Carter C, Tang L, et al. (2004). *BAY 43-9006 exhibits broad spectrum oral antitumor activity and targets the RAF/MEK/ERK pathway and receptor tyrosine kinases involved in tumor progression and angiogenesis*. Cancer Res 64:7099-7109.

We claim:

1. A method of treating gastrointestinal stromal tumors or renal cell carcinoma in a mammal comprising administering a therapeutically effective amount of
    i) an herbal preparation consisting essentially of *Scutellaria baicalensis, Glycyrrhiza uralensis, Ziziphus jujuba*, and *Paeonia lactiflora*; and
    ii) a chemotherapeutic formulation comprising sunitinib or the malate salt of sunitinib.

2. The method of claim 1, wherein the herbal preparation and the chemotherapeutic formulation are administered at separate times.

3. The method of claim 1, wherein the herbal preparation and chemotherapeutic formulation are administered via oral route.

4. The method of claim 1, wherein the herbal preparation consists of *Scutellaria baicalensis, Glycyrrhiza uralensis, Ziziphus jujuba, Paeonia lactiflora*, and one or more pharmaceutically acceptable carriers.

5. The method of claim 1, wherein the chemotherapeutic formulation comprises sunitinib or the malate salt of sunitinib.

6. The method of claim 1, wherein the herbal preparation is administered before the administration of the chemotherapeutic formulation.

7. The method of claim 1, wherein the herbal preparation is administered after the administration of the chemotherapeutic formulation.

8. The method of claim 1, wherein the herbal preparation is administered concurrently with the administration of the chemotherapeutic formulation.

9. A method of relieving side effects of sunitinib or the malate salt of sunitinib in a mammal comprising administering a therapeutically effective amount of
    i) an herbal preparation consisting essentially of *Scutellaria baicalensis, Glycyrrhiza uralensis, Ziziphus jujuba*, and *Paeonia lactiflora*; and
    ii) a chemotherapeutic formulation comprising sunitinib or the malate salt of sunitinib.

10. The method of claim 9, wherein the herbal preparation and the chemotherapeutic formulation are administered at separate times.

11. The method of claim 9, wherein the herbal preparation and chemotherapeutic formulation are administered via oral route.

12. The method of claim 9, wherein the herbal preparation consists of *Scutellaria baicalensis, Glycyrrhiza uralensis, Ziziphus jujuba, Paeonia lactiflora*, and one or more pharmaceutically acceptable carriers.

13. The method of claim 9, wherein the chemotherapeutic formulation comprises sunitinib or the malate salt of sunitinib.

14. The method of claim 9, wherein the herbal preparation is administered before the administration of the chemotherapeutic formulation.

15. The method of claim 9, wherein the herbal preparation is administered after the administration of the chemotherapeutic formulation.

16. The method of claim 9, wherein the herbal preparation is administered concurrently with the administration of the chemotherapeutic formulation.

17. A method of enhancing anticancer activity of sunitinib or the malate salt of sunitinib in a mammal comprising administering a therapeutically effective amount of
    i) an herbal preparation consisting essentially of *Scutellaria baicalensis, Glycyrrhiza uralensis, Ziziphus jujuba*, and *Paeonia lactiflora*; and
    ii) a chemotherapeutic formulation comprising sunitinib or the malate salt of sunitinib.

18. The method of claim 17, wherein the herbal preparation and the chemotherapeutic formulation are administered at separate times.

19. The method of claim 17, wherein the herbal preparation and chemotherapeutic formulation are administered via oral route.

20. The method of claim 17, wherein the herbal preparation consists of *Scutellaria baicalensis, Glycyrrhiza uralensis, Ziziphus jujuba, Paeonia lactiflora*, and one or more pharmaceutically acceptable carriers.

21. The method of claim 17, wherein the chemotherapeutic formulation comprises sunitinib or the malate salt of sunitinib.

22. The method of claim 17, wherein the herbal preparation is administered before the administration of the chemotherapeutic formulation.

23. The method of claim 17, wherein the herbal preparation is administered after the administration of the chemotherapeutic formulation.

24. The method of claim 17, wherein the herbal preparation is administered concurrently with the administration of the chemotherapeutic formulation.

* * * * *